(12) United States Patent
Rantala

(10) Patent No.: US 6,250,302 B1
(45) Date of Patent: Jun. 26, 2001

(54) METHOD AND ARRANGEMENT IN CONNECTION WITH VENTILATOR

(75) Inventor: Börje Rantala, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 0 days.

(21) Appl. No.: 09/185,794

(22) Filed: Nov. 4, 1998

(30) Foreign Application Priority Data

Nov. 5, 1997 (FI) ......................................................... 974148

(51) Int. Cl.$^7$ .............................. A62B 7/00; A62B 9/00; G05B 1/00
(52) U.S. Cl. .............................. 128/205.11; 128/205.13; 128/205.14; 128/204.21; 128/204.28
(58) Field of Search ..................... 128/204.8, 204.21, 128/204.22, 204.23, 204.28, 205.11, 205.13, 205.14, 205.24

(56) References Cited

U.S. PATENT DOCUMENTS

| | | | |
|---|---|---|---|
| 3,307,542 | * 3/1967 | Andreasen | 128/205.28 |
| 3,789,837 | * 2/1974 | Philips et al. | 128/205.28 |
| 3,831,595 | * 8/1974 | Valenta et al. | 128/205.28 |
| 3,850,170 | 11/1974 | Cox . | |
| 3,973,564 | * 8/1976 | Carden | 128/205.28 |
| 4,141,354 | * 2/1979 | Ismach | 128/204.26 |
| 4,186,737 | 2/1980 | Valenta et al. . | |
| 4,256,100 | * 3/1981 | Levy et al. | 128/205.24 |
| 4,567,889 | * 2/1986 | Lehmann | 128/204.28 |
| 4,791,922 | * 12/1988 | Lindsay-Scott et al. | 128/205.28 |
| 4,883,051 | * 11/1989 | Westenskow et al. | 128/204.21 |
| 4,909,246 | * 3/1990 | Kiske et al. | 128/205.14 |
| 4,938,212 | * 7/1990 | Snook et al. | 128/205.24 |
| 4,991,576 | * 2/1991 | Henkin et al. | 128/203.28 |
| 5,072,728 | 12/1991 | Pasternack . | |
| 5,490,499 | * 2/1996 | Heinonen et al. | 128/203.28 |
| 5,651,360 | * 7/1997 | Tobia | 128/204.28 |
| 5,664,563 | 9/1997 | Schroeder et al. . | |
| 5,666,945 | * 9/1997 | Davenport | 128/204.23 |
| 5,839,433 | * 11/1998 | Higenbottam | 128/204.21 |
| 5,979,443 | * 11/1999 | Dingley | 128/204.28 |

FOREIGN PATENT DOCUMENTS

| | | | |
|---|---|---|---|
| 697224 | 2/1996 | (EP) . | |
| 1488358 | 12/1977 | (GB) . | |
| 2211742 | 7/1989 | (GB) . | |
| 96/41651 | * 12/1996 | (WO) | 128/204.28 |

* cited by examiner

Primary Examiner—Aaron J. Lewis
Assistant Examiner—Joseph F. Weiss
(74) Attorney, Agent, or Firm—Andrus, Sceales, Starke & Sawall, LLP

(57) ABSTRACT

A method and arrangement in connection with a ventilator, in which fresh gas is supplied to a patient and part of the patient's breathing gas is supplied to the patient with a bellows means. To provide a basic solution suitable for a variety of uses fresh gas is supplied to the patient by means of a gas mixer. The fresh gas flow from the gas mixer is occasionally led to drive the bellows means.

12 Claims, 4 Drawing Sheets

METHOD AND ARRANGEMENT IN CONNECTION WITH VENTILATOR

BACKGROUND OF THE INVENTION

The invention relates to a method in connection with a ventilator, the method comprising supplying fresh gas to a patient and supplying part of the patient's breathing gas to the patient with a bellows means. The invention also relates to an arrangement in connection with a ventilator.

In the intensive care of patients an open ventilator is conventionally used. In this type of ventilator air and gas are mixed dynamically by means of control valves during a breathing cycle so that the desired tidal volume and oxygen concentration are achieved. The system is open since the gases used are cheap and can be let to the room air after each exhalation. Thus the ventilator and the gas mixer are alternative embodiments of the same valves.

The anaesthetic gases used in an anaesthesia system are both expensive and harmful to the health if let to the room air. For these reasons semi-closed gas circulation is employed in anaesthesia, i.e. a large part of the exhaled gas is returned to the patient after the removal of carbon dioxide. Continuous fresh gas flow refreshes the gas mixture, and excess gas is delivered to a degasification system through an overflow valve. Prior art anaesthesia systems are characterized in that they comprise a separate gas mixer, a separate ventilator, e.g. a pneumatic ventilator or a mechanical piston ventilator, and that fresh gas flow is continuous.

As such the systems described above work well. Usually both of the above-mentioned systems are used in hospitals, often even parallelly. The problem related to this is that the system in its entirety is complex and expensive since there are no common components or groups of components.

BRIEF SUMMARY OF THE INVENTION

The object of the invention is to provide a compact basic solution which may be used both as an intensive care system and as an anaesthesia system with minor adjustments. This is achieved with the method and arrangement of the invention. The method of the invention is characterized in that fresh gas is supplied to a patient by means of a gas mixer and the fresh gas flow from the gas mixer is occasionally led to drive a bellows means. The arrangement of the invention is characterized in that the means that are arranged to supply fresh gas to the patient comprise a gas mixer and that by using a valve device the fresh gas flow from the mixer is occasionally led to drive the bellows means.

First of all, the invention has the advantage that it allows to combine components of intensive care systems and anaesthesia systems, which simplifies the system considerably with respect to the prior art. Due to its simplicity the system is cheaper to implement than the prior art solutions and also very compact, since the ventilator subsystem is combined with the gas mixer subsystem. A further advantage is that it is economical for the producer of the apparatus to maintain and service systems which have many common components. In addition, the apparatus group can be provided with a structure which is more modular that that of traditional anaesthesia and intensive care ventilators.

BRIEF DESCRIPTION OF THE SEVERAL VIEWS OF THE DRAWING

In the following the invention will be described in greater detail by means of prior art embodiments and preferred embodiments of the invention illustrated in the accompanying drawings, in which FIG. 1 schematically illustrates a traditional anaesthesia system.

DETAILED DESCRIPTION OF THE INVENTION

Figure 1:
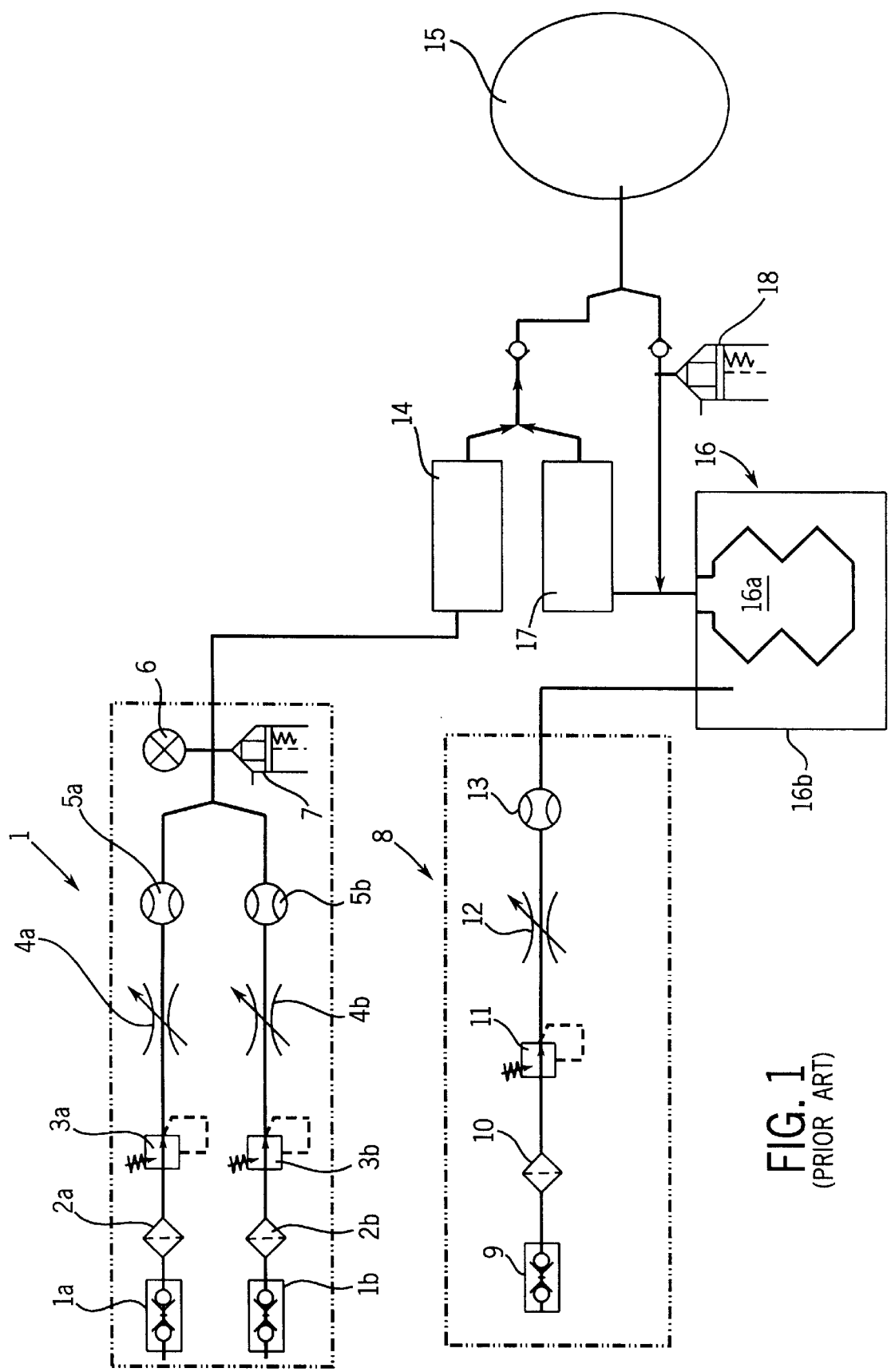

FIG. 1 schematically illustrates a traditional prior art anaesthesia system. The system of FIG. 1 comprises a separate gas mixer 1 and a separate ventilator 8, which in the example of FIG. 1 is a pneumatic ventilator. A mechanical piston ventilator, for example, may naturally be used instead of the pneumatic ventilator.

The gas mixer 1 comprises an inlet connection 1a for air and/or $N_2O$ and another inlet connection 1b for oxygen. The gas mixer further comprises filters 2a, 2b, pressure regulators 3a, 3b, flow controls 4a, 4b and flow meters 5a, 5b. Reference numeral 6 indicates a pressure meter in FIG. 1 and reference numeral 7 a valve member.

The separate ventilator 8 comprises an inlet 9 for air or oxygen, a filter 10, a pressure regulator 11, a flow control 12 and a flow meter 13.

The fresh gas from the gas mixer is led to a patient 15 through an anaesthetic vaporizer 14 in the example of FIG. 1. The outflow from the ventilator 8 is in turn led to drive a bellows means 16. The bellows means 16 comprise a bellows 16a and a container 16b in which the bellows is located. The outflow from the ventilator 8 is led to the container 16b outside the bellows 16a. Most of the gas exhaled by the patient 15 is returned to the patient through a carbon dioxide absorber 17. Continuous fresh gas flow from the gas mixer 1 refreshes the gas mixture, and excess gas is delivered to a degasification system by means of an overflow valve 18.

Figure 2:
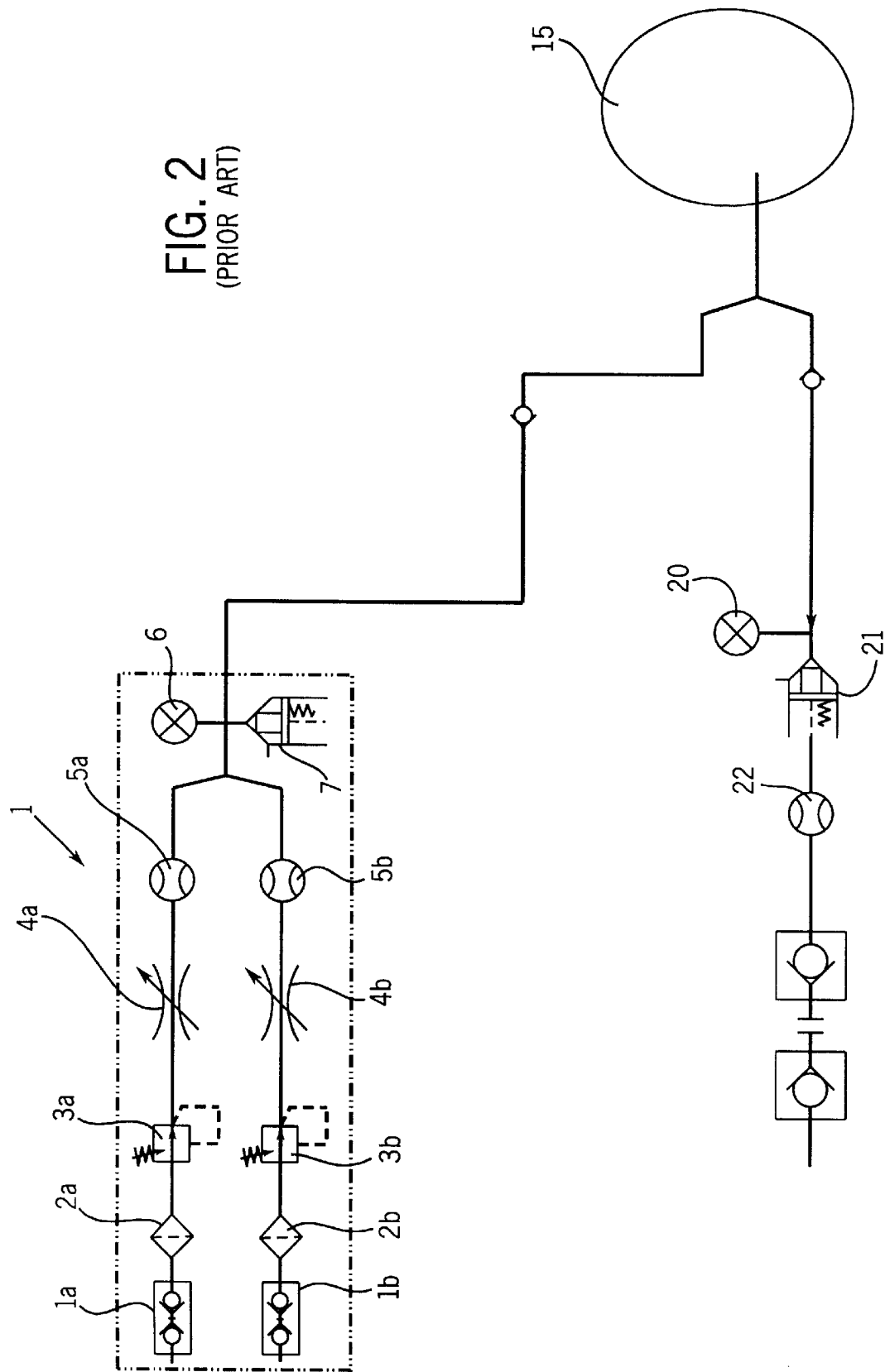
FIG. 2 schematically illustrates a traditional intensive care ventilator.

FIG. 2 schematically illustrates a traditional prior art open ventilator used in intensive care. In this type of ventilator air and oxygen are mixed during a breathing cycle with a control valve so that the desired tidal volume and oxygen concentration are achieved. Air and oxygen are mixed by means of a gas mixer 1. The gas mixer 1 comprises the same main parts as illustrated in FIG. 1. The mixture of gases is supplied to a patient 15 through a unidirectional valve. The gas exhaled by the patient is led to degasification. The exhalation line is provided with a device 22 for measuring the flow, a device 20 for measuring the pressure of the exhaled air, valve members 21, etc.

The devises described above and their function is fully conventional technology to a person skilled in the art, and thus they will not be described in greater detail in this connection.

The object of the invention is to provide, by combining components of intensive care systems and anaesthesia systems, a common basic solution which can be used both as an anaesthesia system and as an intensive care system. In respect of the gas mixer the solution of the invention is based on the intensive care ventilator, since the present solution employs a pneumatic ventilator instead of a separate ventilator employed in the prior art anaesthesia system. The driving pressure of the pneumatic ventilator is generated by means of the gas mixer by leading the outflow from the gas mixer outside the bellows with the ventilator apparatus.

Figure 3:
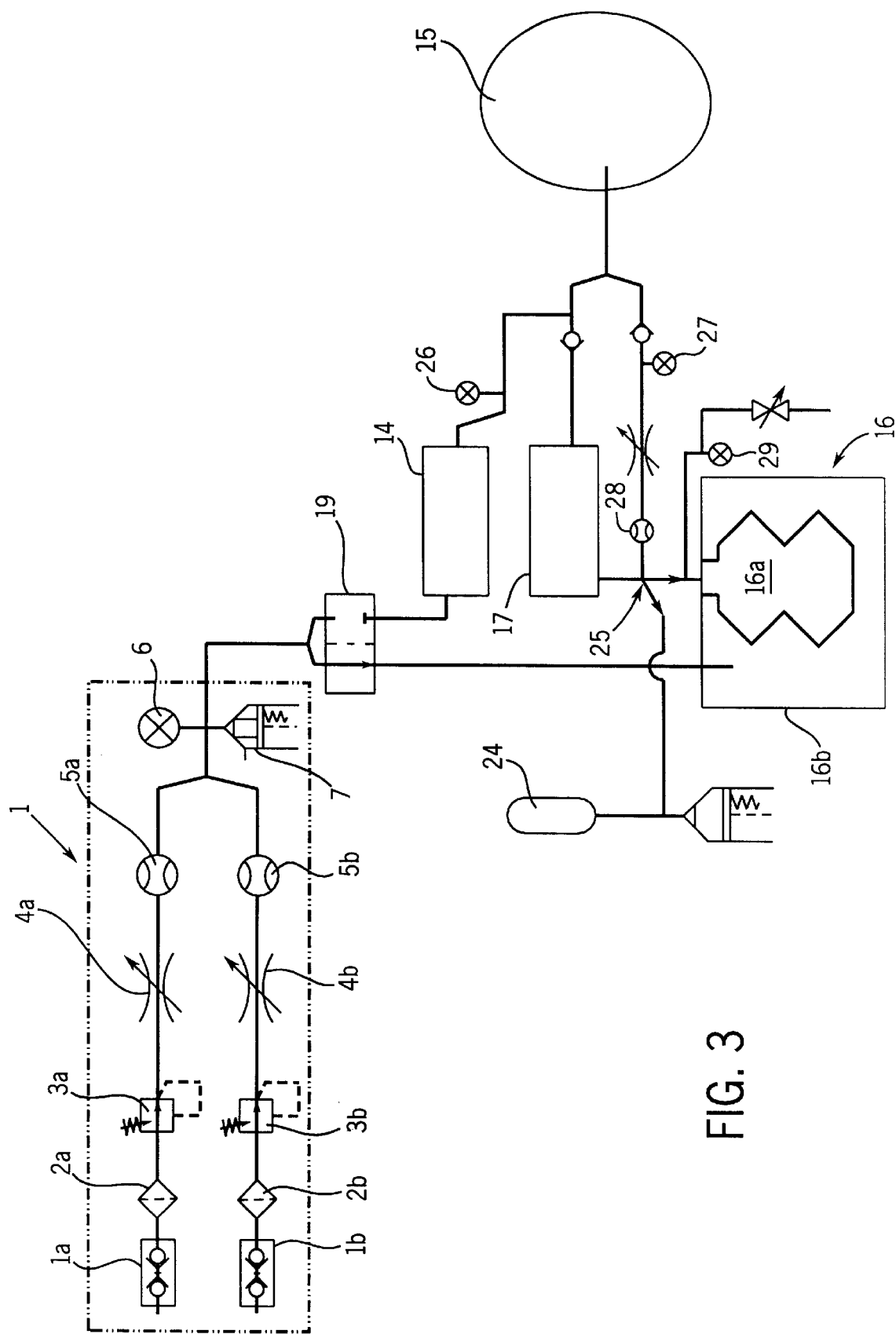
FIG. 3 schematically illustrates the basic idea of the arrangement of the invention, and FIG. 4 schematically illustrates a more detailed embodiment according to the basic idea illustrated in FIG. 3.
Figure 4:
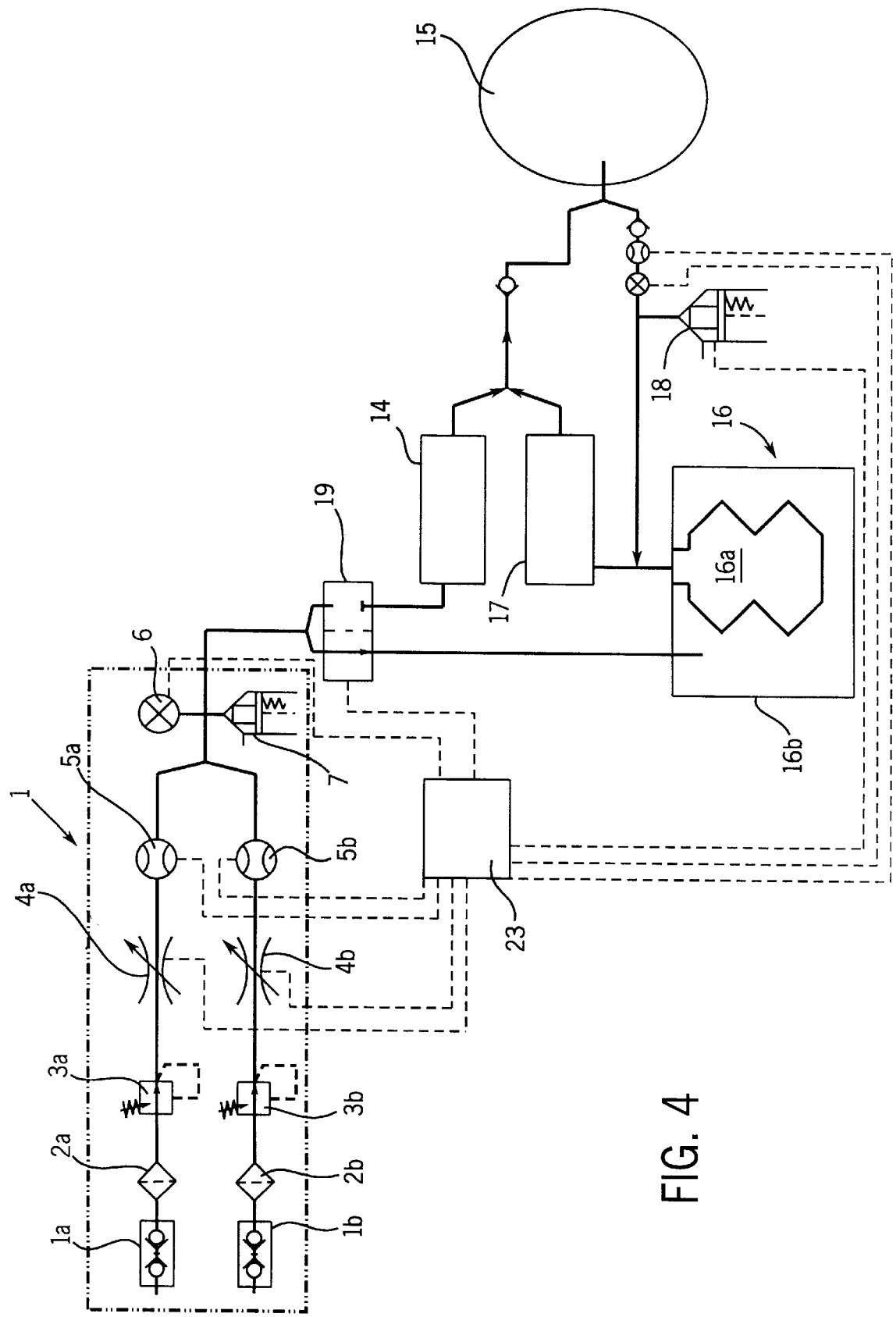

FIG. 3 schematically illustrates the basic idea of the arrangement according to the invention, and FIG. 4 in turn illustrates a preferred embodiment according to the basic idea illustrated in FIG. 3. In FIGS. 3 and 4 the same numbers have the same significance as in FIGS. 1 and 2. An essential feature of the invention is that fresh gas is supplied to the patient 15 by means of the gas mixer I of the intensive care ventilator and that the fresh gas flow from the gas mixer 1 is occasionally led to drive the bellows means 16. The gas mixer comprises the same parts as have been described above for example in connection with FIG. 1. The idea is that the means that are arranged to supply fresh gas to the patient 15 comprise a gas mixer and that by using a valve device 19 the fresh gas flow from the gas mixer 1 is occasionally led to drive the bellows means 16, i.e. to the container 16b outside the bellows 16a. It is particularly advantageous to arrange a valve device 19 to close the duct leading outside the bellows 16a when the valve device 19 guides the flow to the patient 15 and vice versa. Controlling of the valve device 19 can be implemented for example by means of a control device 23. The control device 23 may be any device known per se, such as a microprocessor. The control device 23 may also be part of a larger apparatus which is used for different purposes, e.g. for adjusting different device components. The outflow from the gas mixer 1 can be adjusted so that it contains only air when the outflow is led to drive the bellows means 16. The advantage of the function described above is that only cheap air can be used as the driving gas of the bellows means 16 instead of a mixture of air and oxygen, which is more expensive. For this function the line supplying oxygen can be closed for example by a flow control 4b, whereby the fresh gas flow to the valve device 19 contains only air, as was stated above. The flow control 4b may be controlled for example with the same control device 23 as the valve device 19. Naturally, the flow control 4b may have a control device of its own. Control devices are known in the art, and thus these devices are not described in greater detail in this connection. FIG. 4 schematically illustrates a preferred embodiment of the basic idea of the invention illustrated in FIG. 3, the above-mentioned control device 23 being described in connection with this embodiment. The control device 23 may also control other components of the arrangement and collect data therefrom, as illustrated in FIG. 4. Fresh gas can be supplied to the patient 15 either through an anaesthetic vaporizer 14 or directly to the patient 15 past the anaesthetic vaporizer, depending on the desired mode of use.

In FIG. 3 reference numeral 24 indicates a manual bag and reference numeral 25 a manual/automatic switch. Reference numerals 26 and 27 respectively denote an oxygen detector and a device measuring the exhalation pressure. Reference numerals 28 and 29 respectively denote a device measuring the exhalation flow and a device measuring the pressure of the bellows. The above-mentioned details are conventional technology to a person skilled in the art, and thus they are not described in greater detail in this connection. Some details have been omitted from FIG. 4 for the sake of clarity, since these are not of the essence in view of the inventive concept.

The actual fresh gas flow to the patient is discontinuous. By means of the valve device 19 fresh gas can preferably be supplied to the patient during the inhalation phase. It has been found out to be particularly advantageous to supply fresh gas to the patient during the first part of the inhalation phase, e.g. substantially during 20% of the time used for inhalation. During the rest of the inhalation phase the fresh gas flow is led to drive the bellows means 16. The fresh gas flow to be supplied to the patient can be led through the anaesthetic vaporizer 14, as was stated above. The advantage of this is that the anaesthetic gas is introduced directly into the active part of the patient's 15 lungs and does not remain in the bronchi or in the dead space. Devices for administering other therapeutic agents which need to be carried down to the alveoli may be used together with the anaesthetic vaporizer 14. An example of such an agent is nitrogen oxide. The rest of the inhalation gas is obtained from the bellows 16a through the carbon dioxide absorber 17. The pressure and flow of the air exhaled by the patient may also be measured and data on these may be collected and stored e.g. in the memory of the control device 23, as illustrated in FIG. 4.

The embodiment described above is not intended to restrict the invention in any way, but the invention may be modified quite freely within the scope of the claims. It is thus clear that the arrangement of the invention or its details need not be identical to the those shown in the figures, but other solutions are also possible.

What is claimed is:

1. An apparatus for supplying breathing gas to a patient, the apparatus comprising:

a gas mixer configured to generate a fresh gas flow;

a valve device positioned to receive the fresh gas flow from the gas mixer, the valve device being operable between a first position and a second position;

a ventilator including a bellows connected to the valve device to receive the fresh gas flow from the gas mixer when the valve device is in the second position, wherein the fresh gas flow from the gas mixer drives the bellows such that the bellows generates a ventilator gas flow supplied to the patient as part of the breathing gas; and a control device positioned to operate the valve device between the first position and the second position, wherein the control device moves the valve device to the first position during a first portion of an inhalation phase of each patient breath to divert the fresh gas flow from the gas mixer to the patient and the control device moves the valve device to the second position during a second portion of the inhalation phase of each patient breath to divert the fresh gas flow from the gas mixer to the ventilator to drive the bellows.

2. The apparatus of claim 1 further comprising a sensing device for detecting the respiratory cycle of the patient, the sensing device being connected to the control device to send a signal to the control device indicative of the respiratory cycle of a breath, wherein the control device moves the valve device to the first position during an initial portion of the patient's inhalation phases.

3. The apparatus of claim 2 wherein the control device moves the valve device in the first position during the first 20% of the patient's inhalation phase.

4. The apparatus of claim 1 wherein the gas mixer is connected to a supply of air and a supply of oxygen and the control device is coupled to the gas mixer such that the control device operates the gas mixer such that the fresh gas flow from the gas mixer includes only air when the valve device is in the second position.

5. The apparatus of claim 1 wherein the bellows is adapted to communicate with the patient such that exhaled gas from the patient is received within the bellows.

6. The apparatus of claim 1 further comprising an anesthetic vaporizer connected to the valve device to receive the fresh gas flow from the gas mixer when the valve device is in the first position such that the fresh gas flow is supplied to the patient through the anesthetic vaporizer.

7. A method of supplying breathing gas to a patient during an inhalation phase of each breath, the method comprising the steps of:
   providing a gas mixer to generate a fresh gas flow that forms part of the breathing gas supplied to the patient during the inhalation phase;
   providing a ventilator including a bellows positioned within a bellows container to generate a ventilator gas flow that forms part of the breathing gas supplied to the patient during the inhalation phase;
   positioning a valve device to receive the fresh gas flow from the gas mixer, the valve device being operable between a first position to direct the fresh gas flow to the patient and a second position to direct the fresh gas flow to the bellows container;
   selectively moving the valve device to the first position during a first portion of the inhalation phase of each patient breath to divert the fresh gas flow from the gas mixer to the patient; and
   selectively moving the valve device to the second position during a second portion of the inhalation phase of each patient breath to divert the fresh gas flow from the gas mixer to the bellows container to drive the bellows such that the bellows generates the ventilator gas flow.

8. The method of claim 7 further comprising the step of positioning an anaesthetic vaporizer between the valve device and the patient.

9. The method of claim 7 further comprising the steps of:
   positioning a control device in operative communication with the valve device to control the movement of the valve device between the first position and the second position; and
   positioning a sensing device to detect the respiratory cycle of the patient, the sensing device being coupled to the control unit such that the sensing device sends a signal to the control unit indicative of the respirator cycle, wherein the control device moves the valve device to the first position to supply the the fresh gas flow to the patient during the initial portion of the patient's inhalation phase.

10. The method of claim 9 wherein the valve device is operated to supply the fresh gas flow to the patient during the initial 20% of the patient's inhalation phase.

11. The method of claim 7 wherein the gas mixer is connected to a supply of air and a supply of oxygen, the method further comprising the step of operating the gas mixer such that the fresh gas flow includes only air when the valve device is moved to the second position to divert the fresh gas flow to drive the bellows.

12. The method of claim 7 wherein part of the gas exhaled by the patient is returned to the patient through operation of the bellows.

* * * * *